(12) United States Patent
Porter et al.

(10) Patent No.: US 6,783,659 B2
(45) Date of Patent: *Aug. 31, 2004

(54) PROCESS TO PRODUCE A DILUTE ETHYLENE STREAM AND A DILUTE PROPYLENE STREAM

(75) Inventors: Rodney L. Porter, Pearland, TX (US);
Anne M. Balinsky, Kingwood, TX (US); Eric P. Weber, Kingwood, TX (US)

(73) Assignee: Chevron Phillips Chemical Company, L.P., The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/992,445

(22) Filed: Nov. 16, 2001

(65) Prior Publication Data

US 2003/0094398 A1 May 22, 2003

(51) Int. Cl.[7] .............................................. C10G 69/00
(52) U.S. Cl. ...................... 208/49; 208/211; 585/318; 585/319; 585/329; 585/362
(58) Field of Search .................. 208/49, 211; 585/318, 585/319, 329, 362

(56) References Cited

U.S. PATENT DOCUMENTS

| | | | |
|---|---|---|---|
| 2,372,320 A | 3/1945 | Frey ........................... | 260/671 |
| 2,373,303 A | 4/1945 | Frey et al. ................... | 260/671 |
| 2,415,272 A | 2/1947 | Benedict et al. ............ | 260/668 |
| 2,456,435 A | 12/1948 | Matuszak .................... | 260/345 |
| 2,814,653 A | 11/1957 | Hogan et al. ................ | 260/677 |
| 2,848,522 A | 8/1958 | Gilmore ...................... | 260/683 |
| 3,123,650 A | 3/1964 | Hutson et al. .............. | 260/671 |
| 3,131,230 A | 4/1964 | Hervert et al. ............. | 260/671 |
| 3,200,164 A | 8/1965 | Gerald et al. ............... | 260/671 |
| 3,205,277 A | 9/1965 | Pollitzer et al. ............ | 260/671 |
| 3,437,705 A | 4/1969 | Jones .......................... | 260/671 |
| 3,843,510 A | 10/1974 | Morrison et al. ........... | 208/111 |
| 4,086,288 A | 4/1978 | Irvin et al. .................. | 260/671 |
| 4,107,224 A | 8/1978 | Dwyer ....................... | 260/671 |

(List continued on next page.)

FOREIGN PATENT DOCUMENTS

| | | |
|---|---|---|
| WO | 96/11175 | 4/1996 |
| WO | WO-01/64340 A1 * | 9/2001 |
| WO | 02/29317 | 4/2002 |

OTHER PUBLICATIONS

Pertinent pages of–an Environmental Report dated Apr. 1999 and publicly distributed in Australia by Huntsman Chemical Company.

Hydrocarbon Processing Magazine article, published May 1999, entitled "Integrate ethyl benzene production with an olefins plant".

Oil and Gas Journal Magazine article, published Sep. 26, 1977, entitled "Ehylbenzene Unit operates well on dilute ethylene".

Hydrocarbon Processing Magazine article, published Dec. 1983, entitled "Ethylene From Natural Gas Feedstocks, Part 3, Flow Scheme Comparisons".

Hydrocarbon Processing Magazine article, published Aug. 1979, entitled "Front End Deethanizer Saves Energy".

*Primary Examiner*—Walter D. Griffin
*Assistant Examiner*—James Arnold, Jr.
(74) *Attorney, Agent, or Firm*—Conley Rose, P.C.; Rodney B. Carroll; Joe D. Hulett

(57) ABSTRACT

A process is provided to produce a dilute ethylene stream and a dilute propylene stream to be used as feedstocks for producing olefin-based derivatives. Specifically, the dilute ethylene stream is used as a feedstock to produce ethylbenzene, and the dilute propylene stream is used as a feedstock to produce cumene, acrylic acid, propylene oxide and other propylene based derivatives.

75 Claims, 5 Drawing Sheets

U.S. PATENT DOCUMENTS

| | | | | |
|---|---|---|---|---|
| 4,255,599 A | | 3/1981 | Wu et al. | 585/319 |
| 4,701,190 A | * | 10/1987 | Haehn | 95/161 |
| 5,003,119 A | | 3/1991 | Sardina et al. | 585/323 |
| 5,026,935 A | | 6/1991 | Leyshon et al. | 585/315 |
| 5,026,936 A | | 6/1991 | Leyshon et al. | 585/315 |
| 5,043,506 A | | 8/1991 | Crossland | 585/449 |
| 5,138,113 A | * | 8/1992 | Juguin et al. | 585/322 |
| 5,177,285 A | | 1/1993 | Van Opdorp et al. | 585/467 |
| 5,220,097 A | * | 6/1993 | Lam et al. | 585/809 |
| 5,430,211 A | | 7/1995 | Pogue et al. | 585/323 |
| 5,600,049 A | | 2/1997 | Sy | 585/450 |
| 5,602,290 A | | 2/1997 | Fallon | |
| 5,750,814 A | | 5/1998 | Grootjans et al. | 585/323 |
| 5,750,818 A | | 5/1998 | Mehlberg et al. | 585/709 |
| 5,756,872 A | | 5/1998 | Smith, Jr. et al. | |
| 5,856,607 A | | 1/1999 | Kim | |
| 5,866,734 A | * | 2/1999 | Flick et al. | 585/260 |
| 5,880,320 A | | 3/1999 | Netzer | |
| 5,894,076 A | | 4/1999 | Hearn et al. | 585/251 |
| 5,939,596 A | | 8/1999 | Whitney | 585/259 |
| 5,960,643 A | | 10/1999 | Kuechler et al. | |
| 5,962,758 A | | 10/1999 | Sy et al. | 585/450 |
| 5,977,423 A | | 11/1999 | Netzer | 585/446 |
| 5,981,818 A | | 11/1999 | Purvis et al. | |
| 5,990,370 A | | 11/1999 | Sims | 585/650 |
| 6,002,057 A | | 12/1999 | Hendriksen et al. | 585/448 |
| 6,002,058 A | | 12/1999 | Hearn et al. | 585/448 |
| 6,063,976 A | | 5/2000 | Hendriksen et al. | 585/467 |
| 6,096,935 A | | 8/2000 | Schulz et al. | 585/323 |
| 6,107,533 A | * | 8/2000 | Vebeliunas et al. | 585/259 |
| 6,177,600 B1 | | 1/2001 | Netzer | |
| 6,190,533 B1 | * | 2/2001 | Bradow et al. | 208/57 |
| 6,210,561 B1 | * | 4/2001 | Bradow et al. | 208/89 |
| 6,252,126 B1 | | 6/2001 | Netzer | |
| 6,258,989 B1 | * | 7/2001 | Owen et al. | 585/318 |
| 6,271,433 B1 | | 8/2001 | Keady et al. | 585/802 |
| 6,333,443 B1 | * | 12/2001 | Busson | 585/539 |
| 6,486,369 B1 | * | 11/2002 | Voight et al. | 585/259 |
| 6,677,496 B2 | | 1/2004 | Netzer | 585/648 |

* cited by examiner

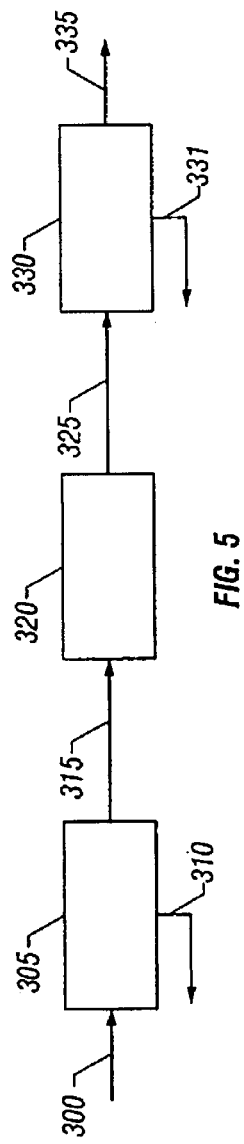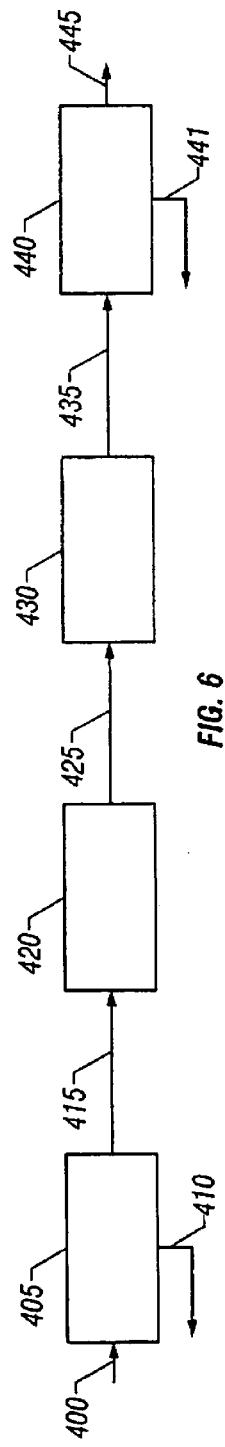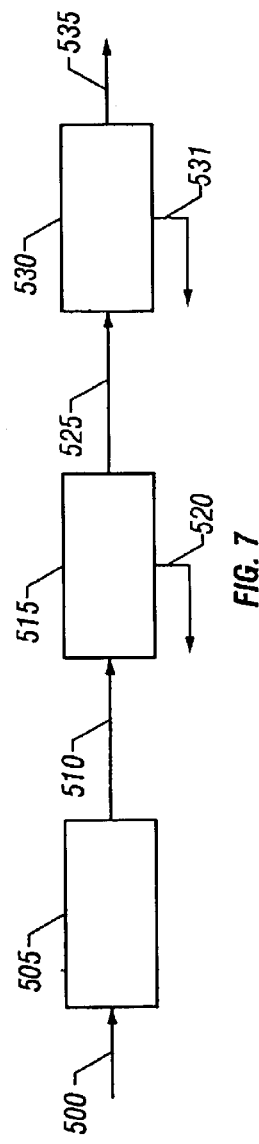

PROCESS TO PRODUCE A DILUTE ETHYLENE STREAM AND A DILUTE PROPYLENE STREAM

FIELD OF THE INVENTION

This invention is related to the field of processes wherein a cracked gas stream is separated to produce dilute olefin streams to be used as feedstocks to produce olefin-based derivatives. Specifically, this invention is related to the field of processes wherein a cracked gas stream is separated to produce a dilute ethylene stream and a dilute propylene stream to be used as feedstocks for producing olefin-based derivatives. More specifically, the dilute ethylene stream is used as a feedstock to produce ethylbenzene, and the dilute propylene stream is used as a feedstock to produce cumene, acrylic acid, propylene oxide or other propylene based derivatives.

BACKGROUND OF THE INVENTION

Feedstock costs in the chemical industry comprise a significant portion of the manufacturing costs. Continuous research is being conducted to lower these costs by utilizing lower cost feed sources. The alkylation of benzene and other aromatics is one area where dilute olefin streams are employed to reduce feed related manufacturing costs. For example, in the production of ethylbenzene, a raw material for the production of styrene, the off-gas from a fluidized catalytic cracking unit (FCC) can be successfully employed as a cost advantaged ethylene source. The FCC off-gas is a dilute stream containing typically less than 30 mole percent ethylene. Due to the large quantities of diluents in the FCC off-gas, such as, for example, hydrogen and methane, the alkylation section of the ethylbenzene unit requires that some of the equipment be oversized. Additionally, the hydrogen sulfide content of the FCC off-gas necessitates its removal in a gas pre-treatment section and subsequent compression before it can be routed to the alkylation reactor. The requirements of having oversized equipment and gas pre-treatment followed by compression greatly increase the capital costs associated with an ethylbenzene unit utilizing FCC off-gas as its feedstock compared to a conventional ethylbenzene unit that utilizes high purity, polymer grade ethylene.

There is a need in the chemical industry to reduce feedstock costs by utilizing dilute olefin streams at olefins-based derivative units rather than polymer grade olefin feedstocks. To fulfill this need, the inventors provide this inventive process. This process reduces the amount of equipment traditionally required for the production of ethylene. An example of some of the equipment that has been eliminated is the ethylene refrigeration compressor, demethanizer, cold box system, and $C_2$ and $C_3$ splitters. Additionally, some equipment is smaller than with conventional crackers of comparable scale. The propylene refrigeration system is reduced in size over that of a conventional cracker.

SUMMARY OF THE INVENTION

An object of this invention is to provide a process to produce a dilute ethylene stream and a dilute propylene stream from a cracked gas stream.

Another object of this invention is to provide a process to produce the dilute ethylene stream and the dilute propylene stream from a cracked gas stream generated by the steam cracking of $C_2$ and higher hydrocarbons.

Another object of this invention is to provide a process to produce the dilute ethylene stream and dilute propylene stream wherein these streams are utilized to produce olefin-based derivatives.

Another object of this invention is to provide a process to produce a dilute ethylene stream wherein the dilute ethylene stream is used as a feedstock to produce ethylbenzene.

Yet another object of this invention is to provide a process to produce a dilute propylene stream wherein the dilute propylene stream is used as a feedstock to produce cumene, acrylic acid, propylene oxide and other propylene derivatives.

In accordance with one embodiment of this invention, a process for producing a dilute ethylene stream and a dilute propylene stream from a cracked gas stream is provided, the process comprising (or optionally, "consisting essentially of" or "consisting of") the following steps in the order named:

(1) separating the cracked gas stream in a deethanizer zone to produce a $C_2-$ stream and a $C_3+$ stream;

(2). hydrogenating the $C_2-$ stream in a hydrogenation zone to remove a portion of the acetylene to produce the dilute ethylene stream;

(3) separating the $C_3+$ stream in a depropanizer zone to produce a $C_3-$ stream and a $C_4+$ stream; and (4) reacting the $C_3-$ stream in a methylacetylene-propadiene hydrogenation (MAPD) reactor zone to convert a portion of methylacetylene and propadiene to propylene and propane to produce the dilute propylene stream.

In accordance with another embodiment of this invention, a process for producing the cracked gas stream is provided, the process comprising (or optionally, "consisting essentially of" or "consisting of"):

(1) heating a hydrocarbon feed in a cracking zone to form a raw cracked gas stream; wherein the raw cracked gas stream comprises hydrogen, methane, $C_2$ hydrocarbons, $C_3$ hydrocarbons and heavier constituents;

(2) quenching the raw cracked gas stream in a quenching zone to produce a quenched, cracked gas stream;

(3) compressing the quenched, cracked gas stream in a first compression zone to form a pressurized, cracked gas stream;

(4) deacidifying the pressurized, cracked gas stream in a deacidifying zone to remove a portion of the hydrogen sulfide to form a wet cracked gas stream; and (5) drying the wet cracked gas stream in a drying zone to reduce the moisture level to form a cracked gas stream.

In accordance with another embodiment of this invention, a process for producing a dilute ethylene stream and a dilute propylene stream is provided, the process comprising (or optionally, "consisting essentially of" or "consisting of") the following steps in the order named:

(1) separating the cracked gas stream in a deethanizer zone to produce a $C_2-$ stream and a $C_3+$ stream;

(2) compressing the $C_2-$ stream in a compression zone to form a pressurized $C_2-$ stream;

(3) hydrogenating the pressurized $C_2-$ stream in a hydrogenation zone to remove a portion of the acetylene to produce the dilute ethylene stream;

(4) separating the $C_3+$ stream in a depropanizer zone to produce a $C_3-$ stream and a $C_4+$ stream; and (5) reacting the $C_3-$ stream in a MAPD reactor zone to convert a portion of methylacetylene and propadiene to propylene and propane to produce the dilute propylene stream.

In accordance with another embodiment of this invention, a process for producing a dilute ethylene stream and a dilute propylene stream is provided, the process comprising (or optionally, "consisting essentially of" or "consisting of") the following steps in the order named:

(1) hydrogenating a portion of the acetylene in the cracked gas stream in a hydrogenation zone to produce a reduced acetylene cracked gas stream;

(2) separating the reduced acetylene cracked gas stream in a deethanizer zone to produce the dilute ethylene stream and a $C_3+$ stream;

(3) separating the $C_3+$ stream in the depropanizer zone to produce a $C_3-$ stream and a $C_4+$ stream; and (4) reacting the $C_3-$ stream in a MAPD reactor zone to convert a portion of methylacetylene and propadiene to propylene and propane to produce the dilute propylene stream.

In accordance with another embodiment of this invention, a process for producing a dilute ethylene stream and a dilute propylene stream is provided, the process comprising (or optionally, "consisting essentially of" or "consisting of") the following steps in the order named:

(1) heating a hydrocarbon feed in a cracking zone to form a raw cracked gas stream; wherein the cracked gas stream comprises hydrogen, methane, $C_2$ hydrocarbons, $C_3$ hydrocarbons and heavier constituents;

(2) quenching the raw cracked gas stream in a quenching zone to produce a quenched, cracked gas stream;

(3) compressing the quenched, cracked gas stream in a first compression zone to form a pressurized cracked gas stream;

(4) deacidifying the pressurized, cracked gas stream in a deacidifying zone to remove a portion of the hydrogen sulfide to form a wet cracked gas stream;

(5) drying the wet cracked gas stream in a drying zone to form a cracked gas stream;

(6) separating the cracked gas stream in a deethanizer zone to produce a $C_2-$ stream and a $C_3+$ stream;

(7) compressing the $C_2-$stream in a second compression zone to form a pressurized $C_2-$ stream;

(8) hydrogenating the pressurized $C_2-$ stream in a hydrogenation zone to remove a portion of the acetylene to produce the dilute ethylene stream; and (9) separating the $C_3+$ stream in a depropanizer zone to produce the dilute propylene stream and a $C_4+$ stream.

(10) reacting the $C_3-$ stream in a MAPD reactor zone to convert a portion of methylacetylene and propadiene to propylene and propane to produce the dilute propylene stream.

In accordance with another embodiment of this invention, a process for producing a dilute ethylene stream and a dilute propylene stream is provided, the process comprising (or optionally, "consisting essentially of" or "consisting of") the following steps in the order named:

(1) heating a hydrocarbon feed in a cracking zone to form a raw cracked gas stream; wherein the cracked gas stream comprises hydrogen, methane, $C_2$ hydrocarbons, $C_3$ hydrocarbons, and heavier constituents;

(2) quenching the raw cracked gas stream in a quenching zone to produce a quenched, cracked gas stream;

(3) compressing the quenched, cracked gas stream in a first compression zone to form a pressurized, cracked gas stream;

(4) deacidifying the pressurized, cracked gas stream in a deacidifying zone to remove a portion of the hydrogen sulfide to form a wet cracked gas stream;

(5) drying the wet cracked gas stream in a drying zone to form a cracked gas stream;

(6) separating the cracked gas stream in a deethanizer zone to produce a $C_2-$ stream and a $C_3+$ stream;

(7) hydrogenating the $C_2-$ stream in a hydrogenation zone to remove a portion of the acetylene to produce the dilute ethylene stream; and (8) separating the $C_3+$ stream in a depropanizer zone to produce the dilute propylene stream and a $C_4+$ stream.

In accordance with another embodiment of this invention, a process for producing a dilute ethylene stream and a dilute propylene stream is provided, the process comprising (or optionally, "consisting essentially of" or "consisting of") the following steps in the order named:

(1) heating a hydrocarbon feed in a cracking zone to form a raw cracked gas stream; wherein the raw cracked gas stream comprises hydrogen, methane, $C_2$ hydrocarbons, $C_3$ hydrocarbons and heavier constituents;

(2) quenching the raw cracked gas stream in a quenching zone to produce a quenched, cracked gas stream;

(3) compressing the quenched, cracked gas stream in a first compression zone to form a pressurized, cracked gas stream;

(4) deacidifying the pressurized, cracked gas stream in a deacidifying zone to remove a portion of the hydrogen sulfide to form a wet cracked gas stream; and (5) drying the wet cracked gas stream in a drying zone to reduce the moisture level to form a cracked gas stream (6) hydrogenating a portion of the acetylene in the cracked gas stream in a hydrogenation zone to produce a reduced acetylene cracked gas stream;

(7) separating the reduced acetylene cracked gas stream in a deethanizer zone to produce the dilute ethylene stream and a $C_3+$ stream;

(8) separating the $C_3+$ stream in the depropanizer zone to produce a $C_3-$ stream and a $C_4+$ stream; and (9) reacting the $C_3-$ stream in a MAPD reactor zone to convert a portion of methylacetylene and propadiene to propylene and propane to produce the dilute propylene stream In accordance with another embodiment of this invention, a process for producing a dilute ethylene stream is provided, the process comprising (or optionally, "consisting essentially of" or "consisting of") the following steps in the order named:

(1) separating the cracked gas stream in a deethanizer zone to produce a $C_2-$ stream and a $C_3+$ stream;

(2). hydrogenating the $C_2-$ stream in a hydrogenation zone to remove a portion of the acetylene to produce the dilute ethylene stream;

(3) routing the $C_3+$ stream to storage or other process unit.

In accordance with another embodiment of this invention, a process for producing a dilute ethylene stream is provided, the process comprising (or optionally, "consisting essentially of" or "consisting of") the following steps in the order named:

(1) separating the cracked gas stream in a deethanizer zone to produce a $C_2-$ stream and a $C_3+$ stream;

(2) compressing the $C_2-$ stream in a compression zone to form a pressurized $C_2-$ stream;

(3) hydrogenating the pressurized $C_2-$ stream in a hydrogenation zone to remove a portion of the acetylene to produce the dilute ethylene stream;

(4) routing the $C_3+$ stream to storage or other process unit.

In accordance with another embodiment of this invention, a process for producing a dilute ethylene stream is provided, the process comprising (or optionally, "consisting essentially of" or "consisting of") the following steps in the order named:

(1) hydrogenating a portion of the acetylene in the cracked gas stream in a hydrogenation zone co produce a reduced acetylene cracked gas stream;

(2) separating the reduced acetylene cracked gas stream in a deethanizer zone to produce the dilute ethylene stream and a $C_3+$ stream;

(3) routing the $C_3+$ stream to storage or other process unit.

In accordance with another embodiment of this invention, a process for producing a dilute ethylene stream and a dilute propylene stream is provided, the process comprising (or optionally, "consisting essentially of" or "consisting of") the following steps in the order named:

(1) heating a hydrocarbon feed in a cracking zone to form a raw cracked gas stream; wherein the cracked gas stream comprises hydrogen, methane, $C_2$ hydrocarbons, $C_3$ hydrocarbons and heavier constituents;

(2) quenching the raw cracked gas stream in a quenching zone to produce a quenched, cracked gas stream;

(3) compressing the quenched, cracked gas stream in a first compression zone to form a pressurized cracked gas stream;

(4) deacidifying the pressurized, cracked gas stream in a deacidifying zone to remove a portion of the hydrogen sulfide to form a wet cracked gas stream;

(5) drying the wet cracked gas stream in a drying zone to produce a cracked gas stream.

(6) separating the cracked gas stream in a deethanizer zone to produce a $C_2-$ stream and a $C_3+$ stream;

(7) compressing the $C_2-$ stream in a second compression zone to form a pressurized $C_2-$ stream;

(8) hydrogenating the pressurized $C_2-$ stream in a hydrogenation zone to remove a portion of the acetylene to produce the dilute ethylene stream; and (9) routing the $C_3+$ stream to storage or other process unit.

In accordance with another embodiment of this invention, a process for producing a dilute ethylene stream is provided, the process comprising (or optionally, "consisting essentially of" or "consisting of"):

(1) heating a hydrocarbon feed in a cracking zone to form a cracked gas stream; wherein the cracked gas stream comprises hydrogen, methane, $C_2$ hydrocarbons, $C_3$ hydrocarbons, and heavier constituents;

(2) quenching the raw cracked gas stream in a quenching zone to produce a quenched, cracked gas stream;

(3) compressing the quenched, cracked gas stream in a first compression zone to form a pressurized cracked gas stream;

(4) deacidifying the pressurized, cracked gas stream in a deacidifying zone to remove a portion of the hydrogen sulfide to form a wet cracked gas stream;

(5) drying the wet cracked gas stream in a drying zone to produce a cracked gas stream;

(6) separating the cracked gas stream in a deethanizer zone to produce a $C_2-$ stream and a $C_3+$ stream;

(7) hydrogenating the pressurized, $C_2-$ stream in the hydrogenation zone to remove a portion of the acetylene to produce the dilute ethylene stream; and (8) routing the $C_3+$ stream to storage or other process unit.

In accordance with another embodiment of this invention, a process for producing a dilute ethylene stream and a dilute propylene stream is provided, the process comprising (or optionally, "consisting essentially of" or "consisting of") the following steps in the order named:

(1) heating a hydrocarbon feed in a cracking zone to form a raw cracked gas stream; wherein the raw cracked gas stream comprises hydrogen, methane, $C_2$ hydrocarbons, $C_3$ hydrocarbons, and heavier constituents;

(2) quenching the raw cracked gas stream in a quenching zone to produce a quenched, cracked gas stream;

(3) compressing the quenched, cracked gas stream in a first compression zone to form a pressurized cracked gas stream;

(4) deacidifying the pressurized, cracked gas stream in a deacidifying zone to remove a portion of the hydrogen sulfide to form a wet cracked gas stream; and (5) drying the cracked gas stream in a drying zone to produce a cracked gas stream.

(6) hydrogenating a portion of the acetylene in the cracked gas stream in a hydrogenation zone to produce a reduced acetylene cracked gas stream;

(7) separating the reduced acetylene cracked gas stream in a deethanizer zone to produce the dilute ethylene stream and a $C_3+$ stream;

(8) separating the $C_3+$ stream in the depropanizer zone to produce a $C_3-$ stream and a $C_4+$ stream; and (9) reacting the $C_3-$ stream in a MAPD reactor zone to convert a portion of methylacetylene and propadiene to propylene and propane to produce the dilute propylene stream.

These objects, and other objects, will become more apparent to others with ordinary skill in the art after reading this disclosure.

BRIEF DESCRIPTION OF THE DRAWINGS

FIG. 5. A diagram for a process to produce dilute ethylene.

FIG. 6. A diagram for a process to produce dilute ethylene with a second compression zone.

FIG. 7. A diagram for a process to produce dilute ethylene with a hydrogenation zone before the deethanizer zone.

DETAILED DESCRIPTION OF THE INVENTION

Figure 1:
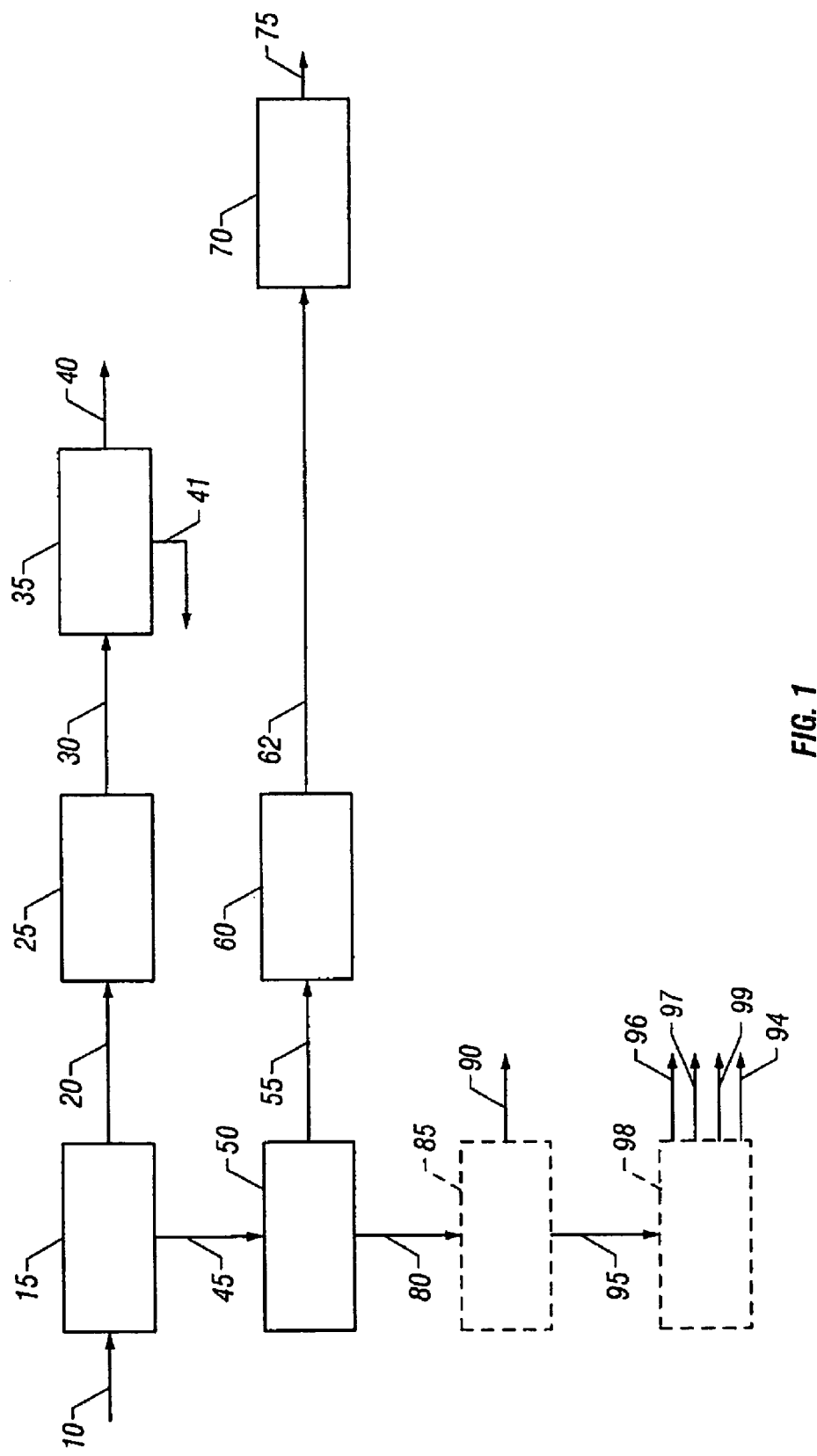
FIG. 1. A diagram showing an embodiment of the process to produce dilute propylene and dilute ethylene.

In a first embodiment of this invention, a process for producing a dilute ethylene stream and a dilute propylene stream from a cracked gas stream is provided as shown in FIG. 1.

Step (1) is separating the cracked gas stream in line 10 in a deethanizer zone 15 to produce a $C_2-$ stream in line 20 and a $C_3+$ stream in line 45. The deethanizer zone 15 comprises a fractionator sufficient to produce the $C_2-$ stream in line 20 and a $C_3+$ stream in line 45. The $C_2-$ stream comprises hydrogen, methane, ethane, acetylene and ethylene. The $C_3+$ stream comprises $C_3$ hydrocarbons and heavier constituents. The cracked gas in line 10 comprises hydrogen, methane, $C_2$ hydrocarbons, $C_3$ hydrocarbons, and heavier constituents, and can be produced by any means known in the art.

Step (2) is hydrogenating the $C_2-$ stream in line 20 in a hydrogenation zone 25 to remove a portion of the acetylene to produce the dilute ethylene stream in line 30. Hydrogenation in the hydrogenating zone 25 can be completed by any means known in the art. For example, an acetylene reactor containing catalyst can be utilized to hydrogenate a portion of the acetylene. Typically, Group VIII metal hydrogenation catalysts are utilized. Hydrogenation catalysts are disclosed in U.S. Pat. Nos. 3,679,762; 4,571,442; 4,347,392; 4,128,595; 5,059,732; 5,488,024; 5,489,565; 5,520,550; 5,583,274; 5,698,752; 5,585,318; 5,587,348; 6,127,310 and 4,762,956; all of which are herein incorporated by reference. Generally, the amount of acetylene remaining in the dilute ethylene stream in line 30 is in a range of less than about 5 ppm by weight, preferably, in a range of 0.5 ppm to 3 ppm by weight.

The temperature and pressure in the hydrogenation zone 25 is that which is sufficient to substantially hydrogenate the acetylene in the $C_2-$ stream in line 20. Preferably, the hydrogenating occurs at a temperature in a range of about 50° F. to about 400° F. and at a pressure in a range of about 350 psia to about 600 psia.

Generally, the amount of ethylene in the dilute ethylene stream in line 30 is in a range of about 30% to about 60% by weight, preferably, 40% to 60% by weight. The dilute ethylene stream in line 30 then can be routed to an dilute ethylene derivative unit 35 to produce different chemicals in line 40 including, but not limited to, ethylbenzene. Preferably, the dilute ethylene stream in line 30 is routed to an ethylbenzene unit. The ethylbenzene unit can utilize any process known in the art. Typically, a Friedel-Crafts alkylation reaction of benzene by ethylene is used. Optionally, a effluent gas stream in line 41 from the dilute ethylene derivative unit 35 can be recycled to a cracking zone 105, shown in FIG. 2, to produce more dilute ethylene. The composition of the effluent gas stream can vary widely depending on the predominant hydrocarbon feed initially fed to the cracking zone. Typically, the effluent gas stream comprises hydrogen, methane, and other light hydrocarbons. Hydrogen and methane may need to be removed from the dilute process stream prior to recycle. This removal can be accomplished by separation membranes, separators, or other equipment.

Step (3) is separating the $C_3+$ stream in line 45 in a depropanizer zone 50 to produce a $C_3-$ stream in line 55 and a $C_4+$ stream in line 80. The depropanizer zone 50 comprises a fractionator sufficient to produce the $C_3-$ stream in line 55 and a $C_4+$ stream in line 80. The $C_3-$ stream in line 55 comprises propane, propylene, methylacetylene and propadiene. The amount of propylene in the $C_3-$ stream in line 55 is in a range of about 55% to about 98% by weight, preferably, in a range of 85% to 96% by weight. The $C_4+$ stream in line 80 comprises $C_4$ hydrocarbons and heavier hydrocarbon constituents.

Step (4) is reacting the $C_3-$ stream in line 55 in a MAPD reactor zone 60 to remove a portion of methylacetylene and propadiene to produce the dilute propylene stream in line 62. The hydrogenation process for the reduction of MAPD occurs in the MAPD reactor zone 60 can be completed by any means known in the art. Generally, the amount of methylacetylene and propadiene remaining in the dilute propylene stream in line 62 is less than 2 ppm by weight.

The dilute propylene stream in line 62 can be routed to an dilute propylene derivative unit 70 to produce different dilute propylene derivatives. For example, the dilute propylene stream in line 62 can be routed to a process to produce cumene, propylene oxide or acrylic acid in line 75. Cumene can be produced by any process known in the art. Typically, a Friedel-Crafts alkylation reaction of benzene by propylene is used to produce cumene. Cumene then can be used to produce other products, such as, for example, phenols.

Optionally, the $C_4+$ stream in line 80 is separated in a debutanizer zone 85 to produce a $C_4$ stream in line 90 and a $C_5+$ stream in line 95. The debutanizer zone 85 comprises a fractionator sufficient to produce the $C_4$ stream in line 90 and a $C_5+$ stream in line 95. The $C_4$ stream in line 90 comprises $C_4$ hydrocarbons. The $C_5+$ stream in line 95 comprises $C_5$ hydrocarbons and heavier hydrocarbon constituents.

Optionally, the $C_5+$ stream in line 95 is treated in a hydrotreating zone 98 to produce a $C_5$ diolefins stream in line 96, a benzene-toluene-xylenes (BTX) stream in line 99, a dicyclopentadiene (DCPD) stream in line 97 and a fuel oil stream in line 94. The treatment of the $C_5+$ stream in the hydrotreating zone 98 can be accomplished by any means known in the art. For example, U.S. Pat. No. 6,258,989 discloses a hydrotreating zone that can be utilized in this invention, herein incorporated by reference. The $C_5$ diolefins stream in line 96 comprises $C_5$ hydrocarbons, and the BTX stream in line 99 comprises benzene, toluene, and xylenes. The DCPD stream in line 97 comprises dicyclopentadiene, and the fuel oil stream in line 94 comprises $C_8+$ hydrocarbons.

Figure 2:
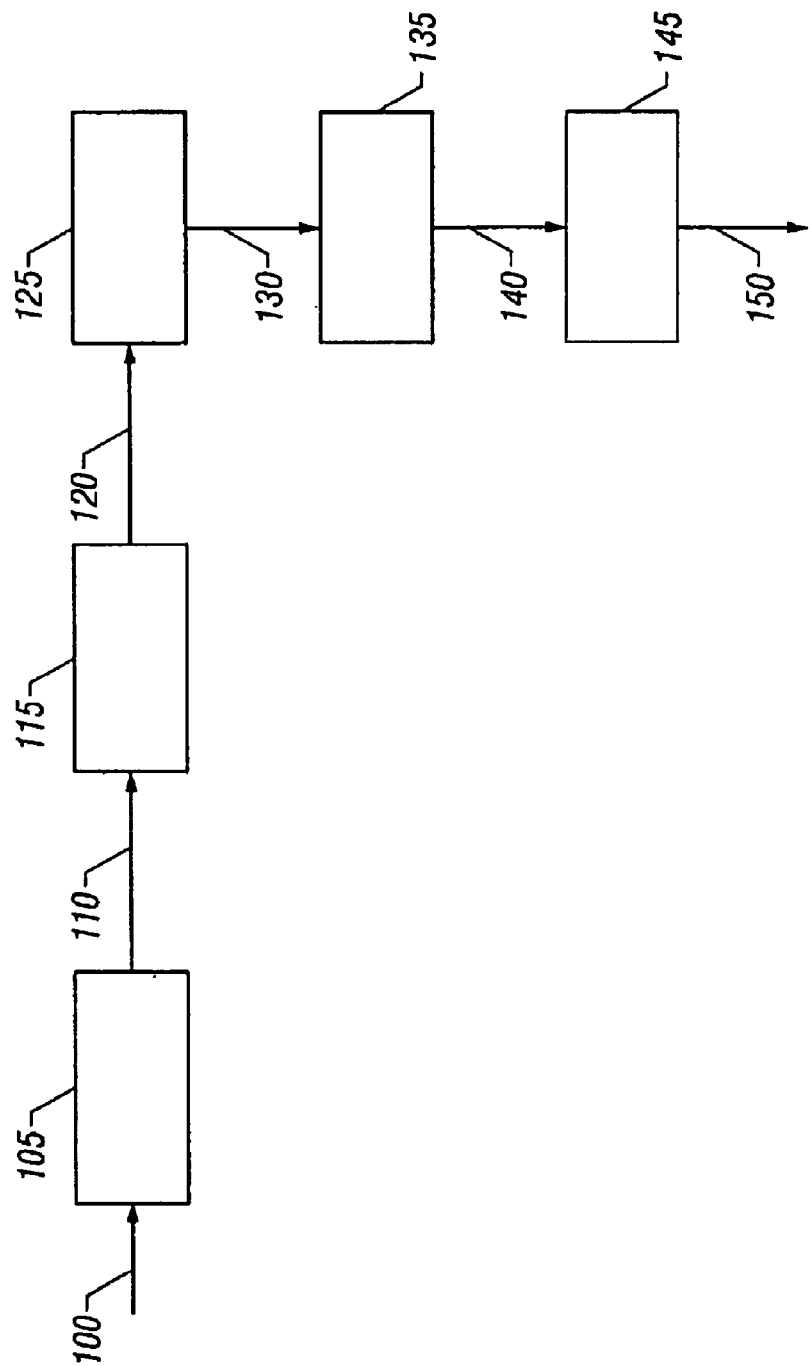
FIG. 2. A diagram showing the preferred method of producing cracked gas feed.

In a second embodiment of the invention, the cracked gas stream utilized as the feedstock in this process can be produced by any process known in the art. A preferred process for producing the cracked gas stream is provided as shown in FIG. 2.

Step (1) is heating a hydrocarbon feed in line 100 in a cracking zone 105 to produce a raw cracked gas stream in line 110. Generally, the hydrocarbon feed in line 100 comprises at least one hydrocarbon selected from the group consisting of ethane, propane, butane, pentane, naphtha, gas condensates, gas oils, and mixtures thereof. Preferably, a majority of the hydrocarbon feed in line 100 consists of $C_5$ hydrocarbons and higher hydrocarbons.

The cracking zone 105 comprises at least one radiant furnace reactor capable of producing the raw cracked gas stream in line 110. Typically, dilution stream is added to the radiant furnace reactors to reduce coking and to reduce the partial pressure of the hydrocarbon feed, thus increasing ethylene yield. Radiant furnace reactors are disclosed in U.S. Pat. Nos. 5,151,158; 4,780,196; 4,499,055; 3,274,978; 3,407,789; and 3,820,955; all of which are herein incorporated by reference.

The raw cracked gas in line 110 comprises hydrogen, methane, $C_2$ hydrocarbons, $C_3$ hydrocarbons, and heavier constituents. Generally, the raw cracked gas stream in line 110 comprises at least about 10% by weight ethylene, preferably, at least about 20% by weight ethylene, and most preferably, at least about 30% by weight ethylene. For example, the raw cracked gas stream in line 110 comprises about 1 to about 5 weight percent hydrogen, about 3 to about 25 weight percent methane, less than 1 weight percent acetylene, about 25 to about 35 weight percent ethylene, about 3 to about 45 weight percent ethane, and up to about 55 weight percent $C_3+$ hydrocarbons, depending on the hydrocarbon feed.

Step (2) is quenching the raw cracked gas stream in line 110 in a quenching zone 115 to produce a quenched, cracked gas stream in line 120. Typically, the raw cracked gas stream in line 110 is quenched in quenching zone 115 to a temperature below which the cracking reaction substantially stops in order to prevent coking. Generally, the raw cracked gas stream in line 110 is cooled to a temperature below about 1100° F. to substantially stop the cracking reaction. Preferably, the raw cracked gas stream in line 110 is cooled to a temperature in a range of about 650 to about 1100° F. Quenching can be effected by any means known in the art. For example, the raw cracked gas stream in line 110 can be passed to a quench boiler and quench tower where fuel oil and dilution stream can be removed. Cooling of a raw cracked gas stream is disclosed in U.S. Pat. Nos. 3,407,798; 5,427,655; 3,392,211; 4,3351,275; and 3,403,722, all herein incorporated by reference.

Step (3) is compressing the quenched, cracked gas stream in line 120 in a first compression zone 125 to produce a pressurized, cracked gas stream in line 130. The pressure of the pressurized, cracked gas stream in line 130 is in a range of about 150 psig to about 650 psig. The first compression zone 125 comprises at least one gas compressor. Any gas compressor known in the art can be utilized.

Step (4) is deacidifying the pressurized, cracked gas stream in line 130 in a deacidifying zone 135 to remove a portion of the hydrogen sulfide and carbon dioxide to form a wet cracked gas stream in line 140. Generally, the wet cracked gas stream in line 140 has a hydrogen sulfide concentration less than about 0.1 ppm by weight, preferably, in a range of 25 to 100 ppb by weight. Generally, the wet cracked gas stream has a carbon dioxide concentration of less than about 5 ppm by weight. The hydrogen sulfide can be removed in the deacidifying zone 135 by any means known in the art. For example, diethanolamine or caustic contactors can be used to remove hydrogen sulfide and carbon dioxide.

Step (5) is drying the wet cracked gas stream in line 140 in a drying zone 145 to produce the cracked gas stream in line 150. Generally, the water content of the cracked gas stream in line 150 is sufficiently dry to prevent downstream operational problems. Preferably, the water content of the cracked gas stream is in line 150 is less than 10 ppm by weight. Drying in drying zone 145 can be accomplished by any means known in the art. For example, molecular sieve beds can be utilized to remove water from the wet cracked gas stream in line 140.

Figure 3:
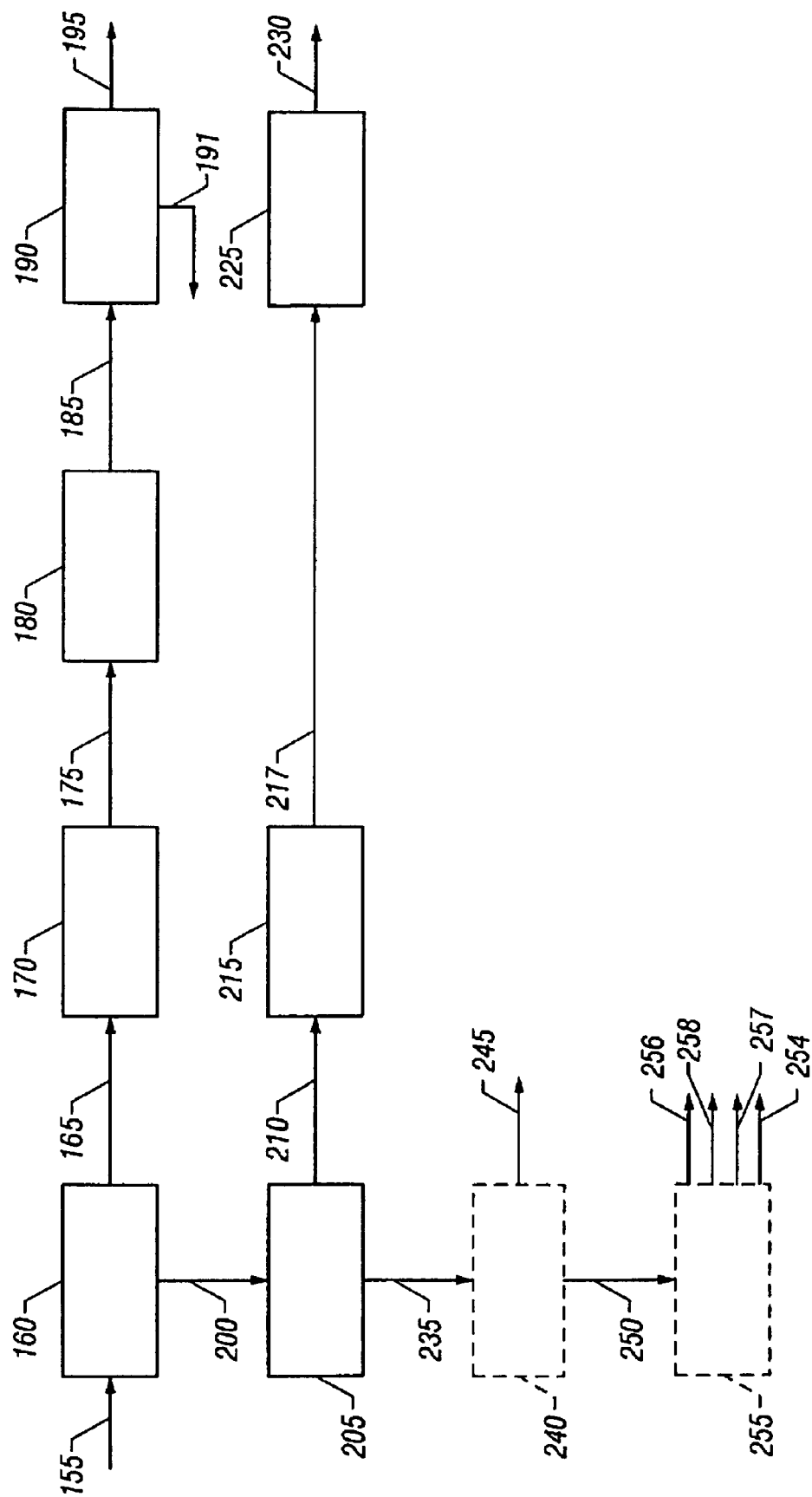
FIG. 3. A diagram showing another embodiment of the process to produce dilute propylene and dilute ethylene with a second compression zone.

In a third embodiment of this invention, a process for producing a dilute ethylene stream and dilute propylene stream from a cracked gas stream is provided as shown in FIG. 3.

Step (1) is separating the cracked gas stream in line 155 in a deethanizer zone 160 to produce a $C_2-$ stream in line 165 and a $C_3+$ stream in line 200. The deethanizer zone 160 comprises a fractionator sufficient to produce the $C_2-$ stream in line 165 and a $C_3+$ stream in line 200. The $C_2$ stream comprises hydrogen, methane, ethane, acetylene and ethylene. The $C_3+$ stream comprises $C_3$ hydrocarbons and heavier constituents.

Step (2) is compressing the $C_2-$ stream in line 165 in a second compression zone 170 to produce a pressurized, $C_2-$ stream in line 175. The pressure of the pressurized, $C_2-$ stream in line 175 is in a range of about 150 to about 650 psig, preferably, in a range of 200 to 650 psig. The second compression zone 170 comprises a gas compressor and related equipment. Any gas compressor known in the art can be utilized.

Step (3) is hydrogenating the pressurized $C_2-$ stream in line 175 in a hydrogenation zone 180 to remove a portion of the acetylene to produce the dilute ethylene stream in line 185. The hydrogenation zone 180 is the same as previously described in the first embodiment.

Generally, the amount of ethylene in the dilute ethylene stream in line 185 is in a range of about 30% to about 60% by weight, preferably, 40% to 60% by weight. The dilute ethylene stream in line 185 then can be routed to an dilute ethylene derivative unit 190 to produce different chemicals in line 195 including, but not limited to, ethylbenzene. The dilute ethylene derivative unit 190 is the same as dilute ethylene derivative unit 35 previously described in the first embodiment. Optionally, an effluent gas stream in line 191 from the dilute ethylene derivative unit 190 can be recycled to a cracking zone 105 in FIG. 2.

Step (4) is separating the $C_3+$ stream in line 200 in a depropanizer zone 205 to produce a $C_3-$ stream in line 210 and a $C_4+$ stream in line 235. The depropanize zone 205 and the $C_3-$ stream and the $C_4+$ stream are the same as previously described in the first embodiment.

Step (5) is reacting the $C_3-$ stream in line 210 in a MAPD reactor zone 215 to remove a portion of methylacetylene and propadiene to produce the dilute propylene stream in line 217. The MAPD reactor zone 215 is the same as MAPD reactor zone 60 previously described in the first embodiment.

The dilute propylene stream in line 217 then can be routed to a dilute propylene derivative unit 225 to produce different dilute propylene derivatives. The dilute propylene derivative unit 225 is the same as dilute propylene derivative unit 70 previously described in the first embodiment.

Optionally, the $C_4+$ stream in line 235 is separated in a debutanizer zone 240 to produce a $C_4$ stream in line 245 and a $C_5+$ stream in line 250. The debutanizer zone 240 comprises a fractionator sufficient to produce the $C_4$ stream in line 245 and a $C_5+$ stream in line 250. The debutanizer zone 240 and the $C_4$ stream in line 245 and the $C_5+$ stream in line 250 are the same as previously described in the first embodiment.

Optionally, treating the $C_5+$ stream is treated in line 250 in a hydrotreating zone 255 to produce a $C_5$ diolefins stream in line 256, a BTX stream in line 257, the DCPD stream in line 258, and a fuel oil stream in line 254. The hydrotreating zone 255, the $C_5$ diolefins stream in line 256, the BTX stream in line 257, and the DCPD stream in line 258 and the fuel oil stream in line 254 are the same as previously described in the first embodiments.

Figure 4:
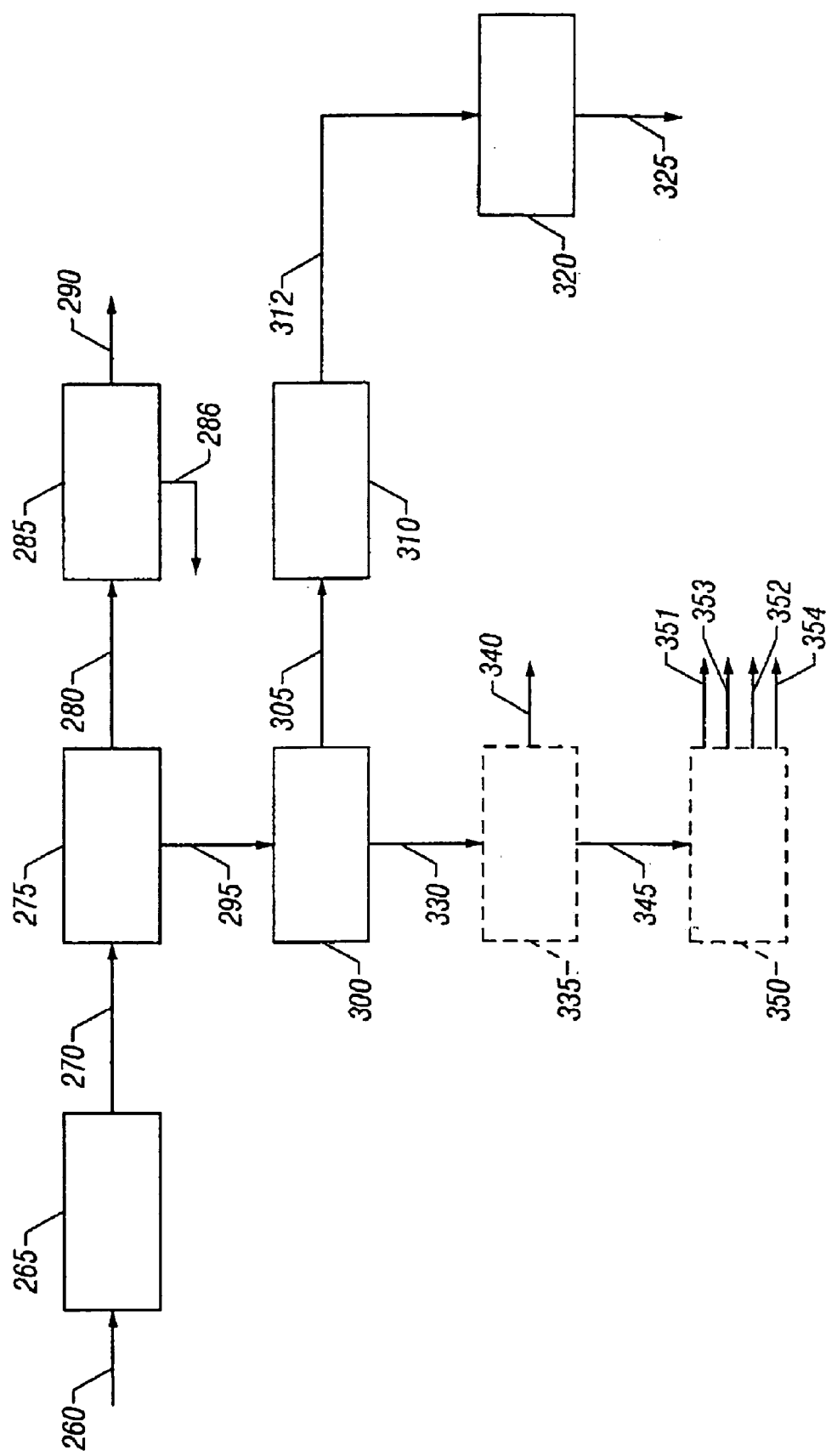
FIG. 4. A diagram showing another embodiment of the process to produce dilute ethylene and dilute propylene with a hydrogenation zone before the deethanizer zone.

In a fourth embodiment of this invention, a process for producing a dilute ethylene and dilute propylene stream from a cracked gas stream is provided as shown in FIG. 4.

Step (1) is hydrogenating the cracked gas stream in line 260 in a hydrogenation zone 265 to remove a portion of the acetylene to produce a reduced acetylene cracked gas stream in line 270. The hydrogenation zone 265 is the same as previously described in the first embodiment.

Step (2) is separating the reduced acetylene cracked gas stream in line 270 in a deethanizer zone 275 to produce the dilute ethylene stream in line 280 and a $C_3+$ stream in line 295. The deethanizer zone 275 comprises a fractionator sufficient to produce the dilute ethylene stream in line 280 and a $C_3+$ stream in line 295. The deethanizer zone 275, dilute ethylene stream in line 280 and $C_3+$ stream in line 295 are the same as previously described in the first and third embodiments.

Generally, the amount of ethylene in the dilute ethylene stream in line 280 is in a range of about 30% to about 60% by weight, preferably, 40% to 60% by weight. The dilute ethylene stream in line 280 then can be routed to an dilute ethylene derivative unit 285 to produce different chemicals in line 290 including, but not limited to, ethylbenzene. The dilute ethylene derivative unit 285 is the same as dilute ethylene derivative unit 35 previously described in the first embodiment. Optionally, an effluent gas stream in line 286 from the dilute ethylene derivative unit 285 can be recycled to a cracking zone 105 in FIG. 2.

Step (3) is separating the $C_3+$ stream in line 295 in a depropanizer zone 300 to produce a $C_3-$ stream in line 305 and a $C_4+$ stream in line 330. The depropanizer zone 300, the $C_3-$ stream in line 305, and the $C_4+$ stream in line 330 are the same as previously described in the first and third embodiments.

Step (4) is reacting the $C_3-$ stream in line 305 in a MAPD reactor zone to remove a portion of methylacetylene and propadiene to produce the dilute propylene stream in line 312. The MAPD reactor zone 310 is the same as previously described in the first and third embodiments.

The dilute propylene stream in line 312 can be routed to a dilute propylene derivative unit 320 to produce different dilute propylene derivatives. The dilute propylene derivative unit 320 is the same as previously described in the first and third embodiments.

Optionally, the $C_4+$ stream in line 330 is separated in a debutanizer zone 335 to produce a $C_4$ stream in line 340 and a $C_5+$ stream in line 345. The debutanizer zone 335 comprises a fractionator sufficient to produce the $C_4$ stream in line 340 and a $C_5+$ stream in line 345. The debutanizer zone 335, the $C_4$ stream in line 340, and the $C_5+$ stream in line 345 are the same as previously described in the first and third embodiments.

Optionally, the $C_5+$ stream is treated in line 345 in a hydrotreating zone 350 to produce a $C_5$ diolefins stream in line 35, a BTX stream in line 352, a DCPD stream in line 353, and a fuel oil stream in line 354. The hydrotreating zone 350, the $C_5$ diolefins stream in line 351, the BTX stream in line 352, the DCPD stream in line 353, and the fuel oil stream in line 354 are the same as previously described in the first and third embodiments.

In a fifth embodiment of this invention, a process for producing a dilute ethylene stream from a cracked gas stream is provided as shown in FIG. 5.

Step (1) is separating the cracked gas stream in line 300 in a deethanizer zone 305 to produce a $C_2-$ stream in line 315 and a $C_3+$ stream in line 310. The deethanizer zone 300 comprises a fractionator sufficient to produce the $C_2-$ stream in line 315 and a $C_3+$ stream in line 310. The $C_2-$ stream comprises hydrogen, methane, ethane, acetylene and ethylene. The $C_3+$ stream comprises $C_3$ hydrocarbons and heavier constituents.

Step (2) is hydrogenating the $C_2-$ stream in line 315 in a hydrogenation zone 320 to remove a portion of the acetylene to produce the dilute ethylene stream in line 325. The hydrogenation zone 320 is the same as previously described in the first embodiment.

Generally, the amount of ethylene in the dilute ethylene stream in line 325 is in a range of about 30% to about 60% by weight, preferably, 40% to 60% by weight. The dilute ethylene stream in line 325 then can be routed to an dilute ethylene derivative unit 330 to produce different chemicals in line 335 including, but not limited to, ethylbenzene. The dilute ethylene derivative unit 330 is the same as dilute ethylene derivative unit 35 previously described in the first embodiment. Optionally, an effluent gas stream in line 331 from the dilute ethylene derivative unit 330 can be recycled to a cracking zone 105 in FIG. 2.

Step (3) is routing the $C_3+$ stream in line 310 to storage or to other process units.

In a sixth embodiment of this invention, a process for producing a dilute ethylene stream from a cracked gas stream is provided as shown in FIG. 6.

Step (1) is separating the cracked gas stream in line 400 in a deethanizer zone 405 to produce a $C_2-$ stream in line 415 and a $C_3+$ stream in line 410. The deethanizer zone 405 comprises a fractionator sufficient to produce the $C_2-$ stream in line 415 and a $C_3+$ stream in line 410. The $C_2-$ stream comprises hydrogen, methane, ethane, acetylene and ethylene. The $C_3+$ stream comprises $C_3$ hydrocarbons and heavier constituents.

Step (2) is compressing the $C_2-$ stream in line 415 in a second compression zone 420 to produce a pressurized, $C_2-$ stream in line 425. The pressure of the pressurized, $C_2-$ stream in line 425 is in a range of about 150 to about 650 psig, preferably, in a range of 200 to 650 psig. The second compression zone 420 comprises a gas compressor and related equipment. Any gas compressor known in the art can be utilized.

Step (3) is hydrogenating the pressurized $C_2-$ stream in line 425 in a hydrogenation zone 430 to remove a portion of the acetylene to produce the dilute ethylene stream in line 435. The hydrogenation zone 430 is the same as previously described in the first embodiment.

Generally, the amount of ethylene in the dilute ethylene stream in line 435 is in a range of about 30% to about 60% by weight, preferably, 40% to 60% by weight. The dilute ethylene stream in line 435 then can be routed to an dilute ethylene derivative unit 440 to produce different chemicals in line 445 including, but not limited to, ethylbenzene. The dilute ethylene derivative unit 440 is the same as dilute ethylene derivative unit 35 previously described in the first embodiment. Optionally, an effluent gas stream in line 441 from the dilute ethylene derivative unit 440 can be recycled to a cracking zone 105 in FIG. 2.

Step (4) is routing the $C_3+$ stream in line 410 to storage or to other process units.

In a seventh embodiment of this invention, a process for producing a dilute ethylene from a cracked gas stream is provided as shown in FIG. 7.

Step (1) is hydrogenating the cracked gas stream in line 500 in a hydrogenation zone 505 to remove a portion of the acetylene to produce a reduced acetylene cracked gas stream in line 510. The hydrogenation zone 505 is the same as previously described in the first and third embodiment.

Step (2) is separating the reduced acetylene cracked gas stream in line 510 in a deethanizer zone 515 to produce the dilute ethylene stream in line 525 and a $C_3+$ stream in line 520. The deethanizer zone 515 comprises a fractionator sufficient to produce the dilute ethylene stream in line 525 and a $C_3+$ stream in line 520. The deethanizer zone 515, dilute ethylene stream in line 525 and $C_3+$ stream in line 520 are the same as previously described in the first and third embodiments.

Generally, the amount of ethylene in the dilute ethylene stream in line 525 is in a range of about 30% to about 60% by weight, preferably, 40% to 60% by weight. The dilute ethylene stream in line 525 then can be routed to an dilute ethylene derivative unit 530 to produce different chemicals in line 535 including, but not limited to, ethylbenzene. The dilute ethylene derivative unit 530 is the same as dilute ethylene derivative unit 35 previously described in the first embodiment.

Step (3) is routing the $C_3+$ stream in line 410 to storage or to other process units.

In another aspect of this invention, the second embodiment which provides a preferred process of producing the cracked gas stream, can be combined with either the first, third, fourth, fifth, sixth or seventh embodiments to yield one continuous process for producing the dilute ethylene stream and dilute propylene stream.

That which is claimed is:

1. A process for producing a dilute ethylene stream and a dilute propylene stream from a cracked gas stream, said process comprising the following steps in the order named:
   (1) separating said cracked gas stream in a deethanizer zone to produce a $C_2-$ stream and a $C_3+$ stream;
   (2). hydrogenating said $C_2-$ stream in a hydrogenation zone to remove a portion of the acetylene to produce said dilute ethylene stream;
   (3) separating said $C_3+$ stream in a depropanizer zone to produce a $C_3-$ stream and a $C_4+$ stream; and
   (4) reacting said $C_3-$ stream in a MAPD reactor zone to convert a portion of methylacetylene and propadiene to propylene and propane to produce said dilute propylene stream.

2. A process according to claim 1 further comprising separating said $C_4+$ stream in a debutanizer zone to produce a $C_4$ stream and a $C_5+$ stream.

3. A process according to claim 1 further comprising passing said dilute ethylene stream to a dilute ethylene derivative unit.

4. A process according to claim 1 wherein said dilute ethylene derivative unit produces ethylbenzene.

5. A process according to claim 1 further comprising passing said dilute propylene stream to a dilute propylene derivative unit.

6. A process according to claim 5 wherein said dilute propylene derivative unit produces cumene, acrylic acid or propylene oxide.

7. A process according to claim 2 further comprising treating said $C_5+$ stream in a hydrotreating zone to produce a $C_5$ diolefins stream, a BTX stream, a DCPD stream and a fuel oil stream.

8. A process according to claim 1 wherein said cracked gas stream is produced by a process comprising:
   (1) heating a hydrocarbon feed in a cracking zone to form a raw cracked gas stream; wherein said raw cracked gas stream comprises hydrogen, methane, $C_2$ hydrocarbons, $C_3$ hydrocarbons and heavier constituents;
   (2) quenching said raw cracked gas stream in a quenching zone to produce a quenched, cracked gas stream;
   (3) compressing said quenched, cracked gas stream in a first compression zone to form a pressurized, cracked gas stream;
   (4) deacidifying said pressurized, cracked gas stream in a deacidifying zone to remove a portion of the hydrogen sulfide to form a wet cracked gas stream; and
   (5) drying said wet cracked gas stream in a drying zone to form a cracked gas stream.

9. A process according to claim 8 wherein said hydrocarbon feed is selected from the group consisting of ethane, propane, butanes, pentanes, naphtha, and mixtures thereof.

10. A process according to claim 8 wherein said hydrocarbon feed consists essentially of $C_5$ hydrocarbons.

11. A process for producing a dilute ethylene stream and a dilute propylene stream from a cracked gas stream, said process comprising the following steps in the order named:
   (1) separating said cracked gas stream in a deethanizer zone to produce a $C_2-$ stream and a $C_3+$ stream;
   (2) compressing said $C_2-$ stream in a compression zone to form a pressurized $C_2-$ stream;
   (3) hydrogenating said pressurized $C_2-$ stream in a hydrogenation zone to remove a portion of the acetylene to produce said dilute ethylene stream;
   (4) separating said $C_3+$ stream in a depropanizer zone to produce a $C_3-$ stream and a $C_4+$ stream; and
   (5) reacting said $C_3-$ stream in a MAPD reactor zone to convert a portion of methylacetylene and propadiene to propylene and propane to produce said dilute propylene stream.

12. A process according to claim 11 further comprising separating said $C_4+$ stream in a debutanizer zone to produce a $C_4$ stream and a $C_5+$ stream.

13. A process according to claim 11 further comprising passing said dilute ethylene stream to a dilute ethylene derivative unit.

14. A process according to claim 13 wherein said dilute ethylene derivative unit produces ethylbenzene.

15. A process according to claim 11 further comprising passing said dilute propylene stream to a dilute propylene derivative unit.

16. A process according to claim 15 wherein said dilute propylene derivative unit produces cumene, acrylic acid, or propylene oxide.

17. A process according to claim 12 further comprising treating $C_5+$ stream in a hydrotreating zone to produce a $C_5$ diolefins stream, a BTX stream, a DCPD stream, and a fuel oil stream.

18. A process according to claim 11 wherein said cracked gas stream is produced by a process comprising:
   (1) heating a hydrocarbon feed in a cracking zone to form a raw cracked gas stream; wherein said raw cracked gas stream comprises hydrogen, methane, $C_2$ hydrocarbons, $C_3$ hydrocarbons, and heavier constituents;
   (2) quenching said raw cracked gas stream in a quenching zone to produce a quenched, cracked gas stream;
   (3) compressing said quenched, cracked gas stream in a first compression zone to form a pressurized cracked gas stream;
   (4) deacidifying said pressurized, cracked gas stream in a deacidifying zone to remove a portion of the hydrogen sulfide to form a wet cracked gas stream; and
   (5) drying said cracked gas stream in a drying zone to produce a cracked gas stream.

19. A process according to claim 18 wherein said hydrocarbon feed is selected from the group consisting of ethane, propane, butanes, pentanes, naphtha, and mixtures thereof.

20. A process according to claim 18 wherein said hydrocarbon feed consists essentially of $C_5$ hydrocarbons.

21. A process for producing a dilute ethylene stream and a dilute propylene stream from a cracked gas stream, said process comprising the following steps in the order named:
   (1) hydrogenating a portion of the acetylene in said cracked gas stream in a hydrogenation zone to produce a reduced acetylene cracked gas stream;

(2) separating said reduced acetylene cracked gas stream in a deethanizer zone to produce said dilute ethylene stream and a $C_3+$ stream;

(3) separating said $C_3+$ stream in said depropanizer zone to produce a $C_3-$ stream and a $C_4+$ stream; and (4) reacting said $C_3-$ stream in a MAPD reactor zone to convert a portion of methylacetylene and propadiene to propylene and propane to produce the dilute propylene stream.

22. A process according to claim 21 further comprising separating said $C_4+$ stream in a debutanizer zone to produce a $C_4$ stream and a $C_5+$ stream.

23. A process according to claim 21 further comprising passing said dilute ethylene stream to a dilute ethylene derivative unit.

24. A process according to claim 21 wherein said dilute ethylene derivative unit produces ethylbenzene.

25. A process according to claim 21 further comprising passing said dilute propylene stream to a dilute propylene derivative unit.

26. A process according to claim 25 wherein said dilute propylene derivative unit produces cumene, acrylic acid, or propylene oxide.

27. A process according to claim 22 further comprising treating $C_5+$ stream in a hydrotreating zone to produce a C5 diolefins stream, a BTX stream, a DCPD stream, and a fuel oil stream.

28. A process according to claim 21 wherein said cracked gas stream is produced by a process comprising:

(1) heating a hydrocarbon feed in a cracking zone to form a raw cracked gas stream;
wherein said raw cracked gas stream comprises hydrogen, methane, $C_2$ hydrocarbons, $C_3$ hydrocarbons, and heavier constituents;

(2) quenching said raw cracked gas stream in a quenching zone to produce a quenched, cracked gas stream;

(3) compressing said quenched, cracked gas stream in a first compression zone to form a pressurized, cracked gas stream;

(4) deacidifying said pressurized, cracked gas stream in a deacidifying zone to remove a portion of the hydrogen sulfide to form a wet cracked gas stream; and (5) drying said cracked stream in a drying zone to produce a cracked gas stream.

29. A process according to claim 25 wherein said hydrocarbon feed is selected from the group consisting of ethane, propane, butanes, pentanes, naphtha and mixtures thereof.

30. A process according to claim 25 wherein said hydrocarbon feed consists essentially of $C_5$ hydrocarbons.

31. A process for producing a dilute ethylene stream and a dilute propylene stream, said process comprising the following steps in the order named:

(1) heating a hydrocarbon feed in a cracking zone to form a raw cracked gas stream; wherein said cracked gas stream comprises hydrogen, methane, $C_2$ hydrocarbons, $C_3$ hydrocarbons and heavier constituents;

(2) quenching said raw cracked gas stream in a quenching zone to produce a quenched, cracked gas stream;

(3) compressing said quenched, cracked gas stream in a first compression zone to form a pressurized cracked gas stream;

(4) deacidifying said pressurized, cracked gas stream in a deacidifying zone to remove a portion of the hydrogen sulfide to form a wet cracked gas stream;

(5) drying said wet cracked gas stream in a drying zone to produce a cracked gas stream;

(6) separating said cracked gas stream in a deethanizer zone to produce a $C_2-$ stream and a $C_3+$ stream;

(7) compressing said $C_2-$ stream in a second compression zone to form a pressurized $C_2-$ stream;

(8) hydrogenating said pressurized $C_2-$ stream in a hydrogenation zone to remove a portion of the acetylene to produce said dilute ethylene stream; and (9) separating said $C_3+$ stream in a depropanizer zone to produce said dilute propylene stream and a $C_4+$ stream;

(10) reacting said $C_3-$ stream in a MAPD reactor zone to convert a portion of methylacetylene and propadiene to propylene and propane to produce said dilute propylene stream.

32. A process according to claim 31 further comprising separating said $C_4+$ stream in a debutanizer zone to produce a $C_4$ stream and a $C_5+$ stream.

33. A process according to claim 32 further comprising treating $C_5+$ stream in a hydrotreating zone to produce a $C_5$ diolefins stream, a BTX stream, a DCPD stream, and a fuel oil stream.

34. A process according to claim 31 further comprising passing said dilute ethylene stream to a dilute ethylene derivative unit.

35. A process according to claim 34 wherein said dilute ethylene derivative unit produces ethylbenzene.

36. A process according to claim 31 further comprising passing said dilute propylene stream to a dilute propylene derivative unit.

37. A process according to claim 36 wherein said dilute propylene derivative unit produces cumene, acrylic acid or propylene oxide.

38. A process according to claim 31 wherein said hydrocarbon feed is selected from the group consisting of ethane, propane, butanes, pentanes, naphtha and mixtures thereof.

39. A process according to claim 31 wherein said hydrocarbon feed consists essentially of $C_5$ hydrocarbons.

40. A process for producing a dilute ethylene stream and a dilute propylene stream, said process comprising the following steps in the order named:

(1) heating a hydrocarbon feed in a cracking zone to form a cracked gas stream; wherein said cracked gas stream comprises hydrogen, methane, $C_2$ hydrocarbons, $C_3$ hydrocarbons, and heavier constituents;

(2) quenching said raw cracked gas stream in a quenching zone to produce a quenched, cracked gas stream;

(3) compressing said quenched, cracked gas stream in a first compression zone to form a pressurized cracked gas stream;

(4) deacidifying said pressurized, cracked gas stream in a deacidifying zone to remove a portion of the hydrogen sulfide to form a wet cracked gas stream;

(5) drying said wet cracked gas stream in a drying zone to produce a cracked gas stream;

(6) separating said cracked gas stream in a deethanizer zone to produce a $C_2-$ stream and a $C_3+$ stream;

(7) hydrogenating said pressurized, $C_2-$ stream in said hydrogenation zone to remove a portion of the acetylene to produce said dilute ethylene stream; and (8) separating said $C_3+$ stream in a depropanizer zone to produce said dilute propylene stream and a $C_4+$ stream;

(9) reacting said $C_3-$ stream in a MAPD zone to convert a portion of methylacetylene and propadiene to propylene and propane to produce said dilute propylene stream.

41. A process according to claim 40 further comprising separating said $C_4+$ stream in a debutanizer zone to produce a $C_4$ stream and a $C_5+$ stream.

42. A process according to claim 40 further comprising treating $C_5+$ stream in a hydrotreating zone to produce a $C_5$ diolefins stream, a BTX stream, a DCPD stream, and a fuel oil stream.

43. A process according to claim 40 further comprising passing said dilute ethylene stream to a dilute ethylene derivative unit.

44. A process according to claim 43 wherein said dilute ethylene derivative unit produces ethylbenzene.

45. A process according to claim 40 further comprising passing said dilute propylene stream to a dilute propylene derivative unit.

46. A process according to claim 45 wherein said dilute propylene derivative unit produces cumene, acrylic acid, or propylene oxide.

47. A process according to claim 40 wherein said hydrocarbon feed is selected from the group consisting of ethane, propane, ethane-propane mix, butanes, pentanes and naphtha and mixtures thereof.

48. A process according to claim 40 wherein said hydrocarbon feed consists essentially of $C_5$ hydrocarbons.

49. A process for producing a dilute ethylene stream and a dilute propylene stream from a cracked gas stream, said process comprising the following steps in the order named:
(1) heating a hydrocarbon feed in a cracking zone to form a raw cracked gas stream; wherein said raw cracked gas stream comprises hydrogen, methane, $C_2$ hydrocarbons, $C_3$ hydrocarbons, and heavier constituents;
(2) quenching said raw cracked gas stream in a quenching zone to produce a quenched, cracked gas stream;
(3) compressing said quenched, cracked gas stream in a first compression zone to form a pressurized cracked gas stream;
(4) deacidifying said pressurized, cracked gas stream in a deacidifying zone to remove a portion of the hydrogen sulfide to form a wet cracked gas stream; and
(5) drying said cracked gas stream in a drying zone to produce a cracked gas stream;
(6) hydrogenating a portion of the acetylene in said cracked gas stream in a hydrogenation zone to produce a reduced acetylene cracked gas stream;
(7) separating said reduced acetylene cracked gas stream in a deethanizer zone to produce said dilute ethylene stream and a $C_3+$ stream;
(8) separating said $C_3+$ stream in said depropanizer zone to produce a $C_3-$ stream and a $C_4+$ stream; and
(9) reacting said $C_3-$ stream in a MAPD reactor zone to convert a portion of methylacetylene and propadiene to propylene and propane to produce the dilute propylene stream.

50. A process according to claim 49 further comprising separating said $C_4+$ stream in a debutanizer zone to produce a $C_4$ stream and a $C_5+$ stream.

51. A process according to claim 49 further comprising passing said dilute ethylene stream to a dilute ethylene derivative unit.

52. A process according to claim 51 wherein said dilute ethylene derivative unit produces ethylbenzene.

53. A process according to claim 49 further comprising passing said dilute propylene stream to a dilute propylene derivative unit.

54. A process according to claim 53 wherein said dilute propylene derivative unit produces cumene, propylene oxide, or acrylic acid.

55. A process according to claim 50 further comprising treating $C_5+$ stream in a hydrotreating zone to produce a $C_5$ diolefins stream, a BTX stream, a DCPD stream, and a fuel oil stream.

56. A process according to claim 49 wherein said hydrocarbon feed is selected from the group consisting of ethane, propane, butanes, pentanes, naphtha and mixtures thereof.

57. A process according to claim 49 wherein said hydrocarbon feed consists essentially of $C_5$ hydrocarbons.

58. A process for producing a dilute ethylene stream and a dilute propylene stream from a cracked gas stream, said process comprising the following steps in the order named:
(1) separating said cracked gas stream in a deethanizer zone to produce a $C_2-$ stream and a $C_3+$ stream;
(2). hydrogenating said $C_2-$ stream in a hydrogenation zone to remove a portion of the acetylene to produce said dilute ethylene stream;
(3) routing said $C_3+$ stream to storage or other process unit.

59. A process according to claim 58 further comprising passing said dilute ethylene stream to a dilute ethylene derivative unit.

60. A process according to claim 59 wherein said dilute ethylene derivative unit produces ethylbenzene.

61. A process for producing a dilute ethylene stream from a cracked gas stream, said process comprising the following steps in the order named:
(1) separating said cracked gas stream in a deethanizer zone to produce a $C_2-$ stream and a $C_3+$ stream;
(2) compressing said $C_2-$ stream in a compression zone to form a pressurized $C_2-$ stream;
(3) hydrogenating said pressurized $C_2-$ stream in a hydrogenation zone to remove a portion of the acetylene to produce said dilute ethylene stream;
(4) routing said $C_3+$ stream to storage or other process unit.

62. A process according to claim 61 further comprising passing said dilute ethylene stream to a dilute ethylene derivative unit.

63. A process according to claim 62 wherein said dilute ethylene derivative unit produces ethylbenzene.

64. A process for producing a dilute ethylene stream from a cracked gas stream, said process comprising the following steps in the order named:
(1) hydrogenating a portion of the acetylene in said cracked gas stream in a hydrogenation zone to produce a reduced acetylene cracked gas stream;
(2) separating said reduced acetylene cracked gas stream in a deethanizer zone to produce said dilute ethylene stream and a $C_3+$ stream;
(3) routing said $C_3+$ stream to storage or other process unit.

65. A process according to claim 64 further comprising passing said dilute ethylene stream to a dilute ethylene derivative unit.

66. A process according to claim 65 wherein said dilute ethylene derivative unit produces ethylbenzene.

67. A process for producing a dilute ethylene stream said process comprising the following steps in the order named:
(1) heating a hydrocarbon feed in a cracking zone to form a raw cracked gas stream; wherein said cracked gas stream comprises hydrogen, methane, $C_2$ hydrocarbons, $C_3$ hydrocarbons and heavier constituents;
(2) quenching said raw cracked gas stream in a quenching zone to produce a quenched, cracked gas stream;

(3) compressing said quenched, cracked gas stream in a first compression zone to form a pressurized cracked gas stream;

(4) deacidifying said pressurized, cracked gas stream in a deacidifying zone to remove a portion of the hydrogen sulfide to form a wet cracked gas stream;

(5) drying said wet cracked gas stream in a drying zone to produce a cracked gas stream;

(6) separating said cracked gas stream in a deethanizer zone to produce a $C_2-$ stream and a $C_3+$ stream;

(7) compressing said $C_2-$ stream in a second compression zone to form a pressurized $C_2-$ stream;

(8) hydrogenating said pressurized $C_2-$ stream in a hydrogenation zone to remove a portion of the acetylene to produce said dilute ethylene stream; and (9) routing said $C_3+$ stream to storage or other process unit.

68. A process according to claim 67 further comprising passing said dilute ethylene stream to a dilute ethylene derivative unit.

69. A process according to claim 68 wherein said dilute ethylene derivative unit produces ethylbenzene.

70. A process for producing a dilute ethylene stream, said process comprising the following steps in the order named:

(1) heating a hydrocarbon feed in a cracking zone to form a cracked gas stream; wherein said cracked gas stream comprises hydrogen, methane, $C_2$ hydrocarbons, $C_3$ hydrocarbons, and heavier constituents;

(2) quenching said raw cracked gas stream in a quenching zone to produce a quenched, cracked gas stream;

(3) compressing said quenched, cracked gas stream in a first compression zone to form a pressurized cracked gas stream;

(4) deacidifying said pressurized, cracked gas stream in a deacidifying zone to remove a portion of the hydrogen sulfide, to form a wet cracked gas stream;

(5) drying said wet cracked gas stream in a drying zone to produce a cracked gas stream;

(6) separating said cracked gas stream in a deethanizer zone to produce a $C_2-$ stream and a $C_3+$ stream;

(7) hydrogenating said pressurized, $C_2-$ stream in said hydrogenation zone to remove a portion of the acetylene to produce said dilute ethylene stream; and (8) routing said $C_3+$ stream to storage or other process unit.

71. A process according to claim 70 further comprising passing said dilute ethylene stream to a dilute ethylene derivative unit.

72. A process according to claim 70 wherein said dilute ethylene derivative unit produces ethylbenzene.

73. A process for producing a dilute ethylene stream, said process comprising the following steps in the order named:

(1) heating a hydrocarbon feed in a cracking zone to form a raw cracked gas stream; wherein said raw cracked gas stream comprises hydrogen, methane, $C_2$ hydrocarbons, $C_3$ hydrocarbons, and heavier constituents;

(2) quenching said raw cracked gas stream in a quenching zone to produce a quenched, cracked gas stream;

(3) compressing said quenched, cracked gas stream in a first compression zone to form a pressurized cracked gas stream;

(4) deacidifying said pressurized, cracked gas stream in a deacidifying zone to remove a portion of the hydrogen sulfide to form a wet cracked gas stream; and (5) drying said cracked gas stream in a drying zone to produce a cracked gas stream;

(6) hydrogenating a portion of the acetylene in said cracked gas stream in a hydrogenation zone to produce a reduced acetylene cracked gas stream;

(7) separating said reduced acetylene cracked gas stream in a deethanizer zone to produce said dilute ethylene stream and a $C_3+$ stream;

(8) routing said $C_3+$ stream to storage or other process unit.

74. A process according to claim 73 further comprising passing said dilute ethylene stream to a dilute ethylene derivative unit.

75. A process according to claim 73 wherein said dilute ethylene derivative unit produces ethylbenzene.

* * * * *